United States Patent [19]

Barner et al.

[11] 4,307,074
[45] Dec. 22, 1981

[54] NOVEL REAGENT

[75] Inventors: Richard Barner, Witterswil; Walter Boguth, Riehen, both of Switzerland

[73] Assignee: Hoffmann-La Roche Inc., Nutley, N.J.

[21] Appl. No.: 75,300

[22] Filed: Sep. 13, 1979

[30] Foreign Application Priority Data

Sep. 18, 1978 [CH] Switzerland .................. 9719/78

[51] Int. Cl.$^3$ .................. G01N 33/48; G01N 33/50; C12Q 1/04
[52] U.S. Cl. .................. 424/13; 23/230 B; 424/8; 424/12
[58] Field of Search .................. 424/8, 12, 13, 199, 424/217, 224; 23/230 B

[56] References Cited

FOREIGN PATENT DOCUMENTS 176298 10/1953 Austria .................. 424/13

OTHER PUBLICATIONS

Haas, Nature, vol. 206, 1965 p. 935.
Faure, Chem. Abs., vol. 58, 1963, p. 14563j.
Inoue et al., Chem. Pharm. Bull. Japan vol. 11, 1963, pp. 1150-1156.

*Primary Examiner*—Anna P. Fagelson
*Attorney, Agent, or Firm*—Jon S. Saxe; George M. Gould; John B. Wilson

[57] ABSTRACT

Novel reagents for the determination of Wassermann antibodies comprising a compound selected from those represented by the formula

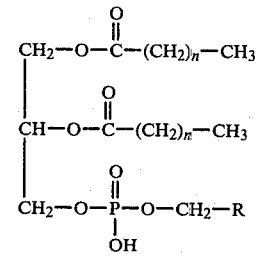

wherein
n is a whole number from 12 to 16 inclusive and
R is phenyl or substituted phenyl and salts thereof.

10 Claims, No Drawings

NOVEL REAGENT

BACKGROUND OF THE INVENTION

The detection of syphilis by the determination of Wassermann antibodies in physiological fluids, particularly in serum is carried out on a large scale. Such determination is particularly important for the control of blood and serum utilized for transfusions.

It is known that cardiolipin, a natural phospholipid extracted from ox heart muscle, can be utilized as a hapten for the serological detection of Wassermann antibodies. Cardiolipin has the general formula

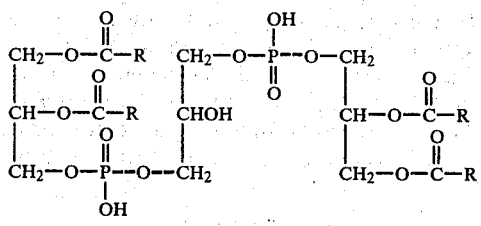

wherein

represents an unsaturated fatty acid residue. Attempts to replace cardiolipin with analogue which might have a simpler structure and, therefore, could be synthesized have not been satisfactory. Until now, such analogues as have been synthesized have demonstrated little or no activity in the serological syphilis test in comparison with cardiolipin as is reported, for example, in Nature, Vol. 206, p. 935 (1965). Suitable analogues of cardiolipin are provided in accordance with the present invention.

DETAILED DESCRIPTION OF THE INVENTION

In accordance with the present invention, easily synthesizable compounds suitable for the detection of syphilis by determination of the Wassermann antibodies are provided. The compounds of the present invention are represented by the following formula

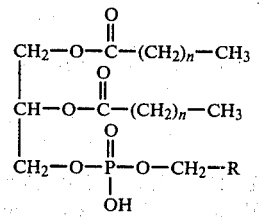

wherein n is a whole number from 12 to 16 inclusive and R is phenyl or substituted phenyl and salts thereof. The compounds of formula I and a suitable adjuvant comprise a reagent for the detection of Wassermann antibodies.

In accordance with the present invention, the term "substituted phenyl" indicates a phenyl radical containing one or more halogen, lower alkyl, trifluoromethyl, lower alkoxy, nitro or cyano substituents. The term "halogen" includes all four halogens, i.e., fluorine, chlorine, bromine, and iodine. The term "lower alkyl" includes both straight-and branched-chain hydrocarbon groups containing 1 to 6 carbon atoms, such as, for example, methyl, ethyl, isopropyl, and the like. The term "lower alkoxy" includes straight-or branched chain alkoxy groups containing from 1 to 6 carbon atoms, such as, for example, methoxyl, ethoxy, and the like.

The salts of the compounds of formula I include all water-soluble salts, particularly alkali metal salts, such as the sodium or potassium salt, alkaline earth metal salts, such as the calcium, magnesium or barium salts, preferably the calcium salt, ammonium and substituted ammonium salts, and the like.

Preferred compounds in accordance with the present invention are those compounds of formula I wherein n is 14 and R is phenyl and water-soluble salts thereof, i.e., D,L-(2,3-di-O-palmitoylglycerol)benzylphosphoric acid, sodium D,L-(2,3-di-O-palmitoylglycerol)benzylphosphoric acid, potassium D,L-(2,3-di-O-palmitoylglycerol)benzylphosphoric acid, calcium D,L-(2,3-di-O-palmitoylglycerol)benzylphosphoric acid and magnesium D,L-(2,3-di-O-palmitoylglycerol)benzylphosphoric acid.

Sodium D,L-(2,3-di-O-palmitoylglycerol)benzylphosphoric acid is especially preferred. This compound is described in Chem. Pharm. Bull (Tokyo) 11, 1150 (1963) as an intermediate in the manufacture of cardiolipin analogues. However, this literature reference contains no indication that this compound would possess reactivity with Wassermann antibodies and, therefore, be useful in a syphilis test.

The compounds of formula I are prepared according to conventional procedures as is known in the literature.

Accordingly, for example, a compound of the formula

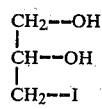

is acylated by reaction with a compound of the formula

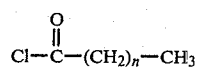

to yield a compound having the formula

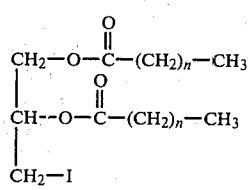

which is in turn phosphorylated by reaction with a compound having the formula

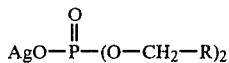

to yield a compound having the formula

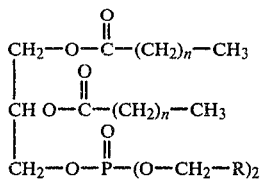

the compound of formula VI is then subjected to anionic monodebenzylation to yield the corresponding compound of formula I. In the above sequence, n and R have the meanings given for formula I.

The compounds of formula I are substantially simpler in structure than cardiolipin. They are easily synthesized and can be used as racemates without further resolution. They are additionally advantageous over cardiolipin in a number of respects. First, the compounds of formula I possess good water solubility, and aqueous solutions thereof exhibit good stability. Further, the compounds of formula I are readily purified by crystallization. Finally, the compounds of formula I can be stored at ambient temperatures without requiring special protective measures, whereas cardiolipin, in contrast, must be stored in a refrigerator under a nitrogen atmosphere.

Reagents suitable for the determination of Wassermann antibodies are prepared in accordance with the present invention by mixing a compound of formula I with a suitable adjuvant or carrier, respectively.

A preferred adjuvant or carrier material, respectively in accordance with the present invention is a mixture of lecithin, preferably egg lecithin, and cholesterol.

For the determination of Wassermann antibodies, the reagent of the invention is mixed with the fluid sample, preferably a serum sample, and the intensity of the immunological reaction, i.e., flocculation, is measured. The ratio of sample to reagent can vary, but preferably is between about 1 to 1 and about 5 to 1, most preferably at about 2.5 to 1.

Wherein the carrier or adjuvant, respectively, for the reagent in accordance with the present invention is a mixture of lecithin and cholesterol, the determination of Wassermann antibodies is carried out by mixing a compound of formula I therewith, adding the sample thereto, and observing the extent of the flocculation. The compound of formula I is preferably mixed with the carrier or adjuvant, respectively, in the presence of a water-miscible inert organic solvent, such as, for example, tetrahydrofuran or a lower alkanol, such as ethanol and a physiological sodium chloride solution. There is thus-obtained a milky suspension having particles a few microns in size.

In the above suspension, the compound of formula I is present in a concentration of from about 0.02 to about 0.20 mg/ml, most preferably from about 0.05 to about 0.10 mg/ml. The concentration of lecithin in this mixture is preferably from about 0.15 to about 0.3 mg/ml, most preferably about 0.25 mg/ml. The concentration of cholesterol in this mixture is preferably from about 0.8 to about 1.2 mg/ml, most preferably about 0.9 mg/ml. The part by volume of the physiological sodium chloride solution in this mixture preferably comprises from about 85% to about 95% by volume, 90% being particularly preferred. The inert organic solvent in this mixture preferably comprises from about 5% and about 15%, most preferably about 10% by volume.

The determination of Wassermann antibodies is measured by the intensity of the immunological reaction, i.e., the degree of flocculation occuring after a reagent such as described above is added to the sample to be tested. Preferably, the extent of flocculation is determined by observing the floc size under a microscope from about 2 to 10 minutes after addition of the sample to the reagent.

The compounds of formula I may be stored in solution, for example, in a hydroalcoholic solution or in solid, i.e., dry form as a crystalline powder. In a reagent kit, they are preferably packaged in solid form in a first container. Packaged in additional containers is the carrier material or adjuvant, respectively, preferably lecithin and cholesterol, and, if desired, control serum.

The following example further illustrates the invention.

EXAMPLE

An ethanolic solution of sodium D,L-(2,3-di-O-palmitoylglycerol)benzylphosphoric acid (1.0 mg/ml), egg lecithin (2.5 mg/ml ) and cholesterol (9.0 mg/ml) was mixed in the ratio 1:9 with a physiological sodium chloride solution to yield a milky suspension containing particles which are of a few $\mu$m in size. 20 $\mu$l of this reagent was stirred with 50 $\mu$l of serum and rocked on a test plate for 4 minutes. The particles aggregated, thus indicating a syphilis-positive serum. The reading-off of the floc size was carried out under a microscope (50×). This methodology represents a convenient semi-quantitative detection of syphilis.

What is claimed is:

1. A reagent for determination of Wassermann antibodies, said reagent comprising an adjuvant comprising a mixture of lecithin and cholesterol, and a compound represented by the formula

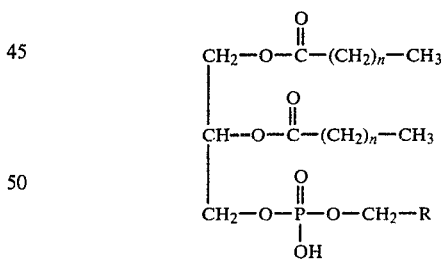

wherein
n is a whole number from 12 to 16 inclusive
and R is phenyl or substituted phenyl and salts thereof.

2. A reagent in accordance with claim 1 wherein said compound is sodium D,L-(2,3-di-O-palmitoylglycerol)-benzylphosphoric acid.

3. A reagent in accordance with claim 1 wherein said lecithin is egg lecithin.

4. A reagent in accordance with claim 1 further comprising a solution of said compound and said adjuvant in a lower alkanol.

5. A reagent in accordance with claim 4 wherein said lower alkanol is ethanol.

6. A reagent in accordance with claim 4 wherein said compound is present in a concentration of from about 0.02 mg/ml to about 0.20 mg/ml and said adjuvant comprises from about 0.1 mg/ml to about 0.3 mg/ml lecithin and from about 0.8 mg/ml to about 1.2 mg.ml cholesterol.

7. A reagent in accordance with claim 4 wherein said compound is present in from about 0.05 mg/ml to about 0.10 mg/ml and said adjuvant comprises about 0.25 mg/ml lecithin and 0.9 mg/ml cholesterol.

8. A method for the determination of Wassermann antibodies in a sample which comprises mixing said sample with the reagent of claim 1 and measuring the intensity of the immunological reaction.

9. A method in accordance with claim 8 wherein said sample is a serum sample, and the ratio of sample to said reagent is from about 1 to 1 to about 5 to 1.

10. A method in accordance with claim 9 wherein said ratio of sample to reagent is about 2.5 to 1.

* * * * *